US008093057B2

(12) United States Patent
Choi et al.

(10) Patent No.: US 8,093,057 B2
(45) Date of Patent: Jan. 10, 2012

(54) SYSTEM FOR QUANTITATIVE MEASUREMENT OF GLYCOHEMOGLOBIN AND METHOD FOR MEASURING GLYCOHEMOGLOBIN

(75) Inventors: Eui Yul Choi, Chuncheon-si (KR); Kie Bong Nahm, Seoul (KR); Jae Hoon Kim, Yongin-si (KR); Dong Seok Jeong, Chuncheon-si (KR); Sang Yeol Park, Chuncheon-si (KR); Joung Dae Moon, Chuncheon-si (KR); Jin Ha Jung, Chuncheon-si (KR); Young Min Kim, Chuncheon-si (KR); So Young Jung, Chuncheon-si (KR); Ae Kyung Park, Chuncheon-si (KR); Byeong Chul Kim, Chuncheon-si (KR); Sung Joong Kim, Chuncheon-si (KR)

(73) Assignee: Boditechmed Inc., Chuncheon-Si, Gangwon-Do (KR)

( * ) Notice: Subject to any disclaimer, the term of this patent is extended or adjusted under 35 U.S.C. 154(b) by 0 days.

(21) Appl. No.: 12/851,477

(22) Filed: Aug. 5, 2010

(65) Prior Publication Data

US 2010/0323450 A1    Dec. 23, 2010

Related U.S. Application Data

(63) Continuation of application No. PCT/KR2008/006306, filed on Oct. 24, 2008.

(51) Int. Cl.
*G01N 33/72* (2006.01)
*G01N 21/76* (2006.01)
*G01N 21/77* (2006.01)

(52) U.S. Cl. .............. 436/67; 436/63; 436/66; 436/164; 436/165; 436/169; 436/172; 436/514; 436/518; 436/535; 436/541; 422/400; 422/420; 422/82.05; 422/82.08; 435/7.1; 435/287.1; 435/287.2; 435/287.7; 435/288.7

(58) Field of Classification Search .................... 436/63, 436/66, 67, 164, 165, 169, 172, 180, 514, 436/518, 535, 541; 422/400, 420, 69, 82.05, 422/82.08; 435/7.1, 287.1, 287.2, 287.7, 435/288.3, 288.7

See application file for complete search history.

(56) References Cited

U.S. PATENT DOCUMENTS 4,647,654 A    3/1987 Knowles et al.
6,174,734 B1 *  1/2001 Ito et al. ................... 436/518

(Continued)

FOREIGN PATENT DOCUMENTS

JP        08-285850 A    11/1996

(Continued)

OTHER PUBLICATIONS

Stivers et al. Diabetes Technology & Therapeutics, vol. 2, No. 4, 2000, pp. 517-526.*

(Continued)

*Primary Examiner* — Maureen Wallenhorst
(74) *Attorney, Agent, or Firm* — Knobbe, Martens, Olson & Bear, LLP

(57) ABSTRACT

The present disclosure provides a device for simultaneously detecting hemoglobin and glycohemoglobin in blood. The device includes a lateral flow assay strip, a laser-induced epifluorescence detection device, and an LED detection device. The present disclosure further provides a method for simultaneously quantifying hemoglobin and glycohemoglobin in blood by an immunological method using the same.

19 Claims, 5 Drawing Sheets

Integrated quantitative assay system for measurement of glycohemoglobin

U.S. PATENT DOCUMENTS

| | | | |
|---|---|---|---|
| 6,677,158 B2* | 1/2004 | Hud et al. | 436/67 |
| 7,195,923 B2* | 3/2007 | McCroskey et al. | 436/87 |
| 7,695,973 B2* | 4/2010 | McCroskey et al. | 436/87 |
| 2002/0173044 A1* | 11/2002 | Pachl et al. | 436/67 |
| 2006/0148096 A1* | 7/2006 | Jina | 436/514 |

FOREIGN PATENT DOCUMENTS

| | | |
|---|---|---|
| JP | 2002-303629 | 10/2002 |
| JP | 2007-003411 A | 1/2007 |
| KR | 2004-0018893 | 3/2004 |
| KR | 10-2006-0023098 | 3/2006 |
| KR | 10-0639776 | 10/2006 |
| WO | WO 2005/066624 | 7/2005 |

OTHER PUBLICATIONS

International Search Report for PCT/KR2008/006306 dated Jun. 4, 2009.

Written Opinion for PCT/KR2008/006306 dated Jun. 4, 2009.

Office Action dated Oct. 17, 2011 of Japanese Patent Application No. 2010-541385.

* cited by examiner

[FIG. 1]
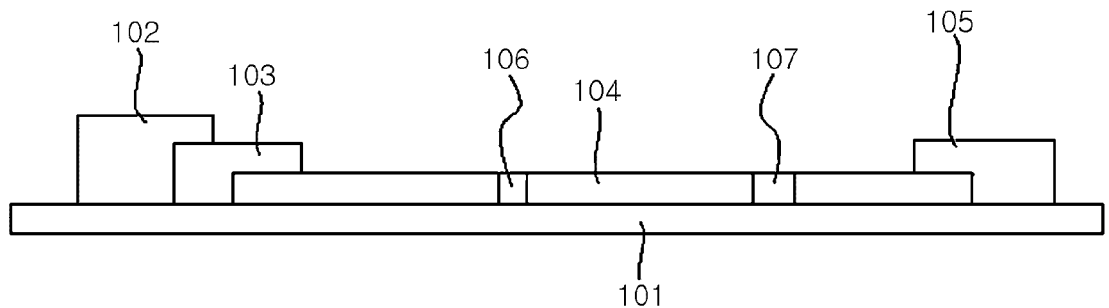
Lateral flow quantitative assay strip
[FIG. 2]
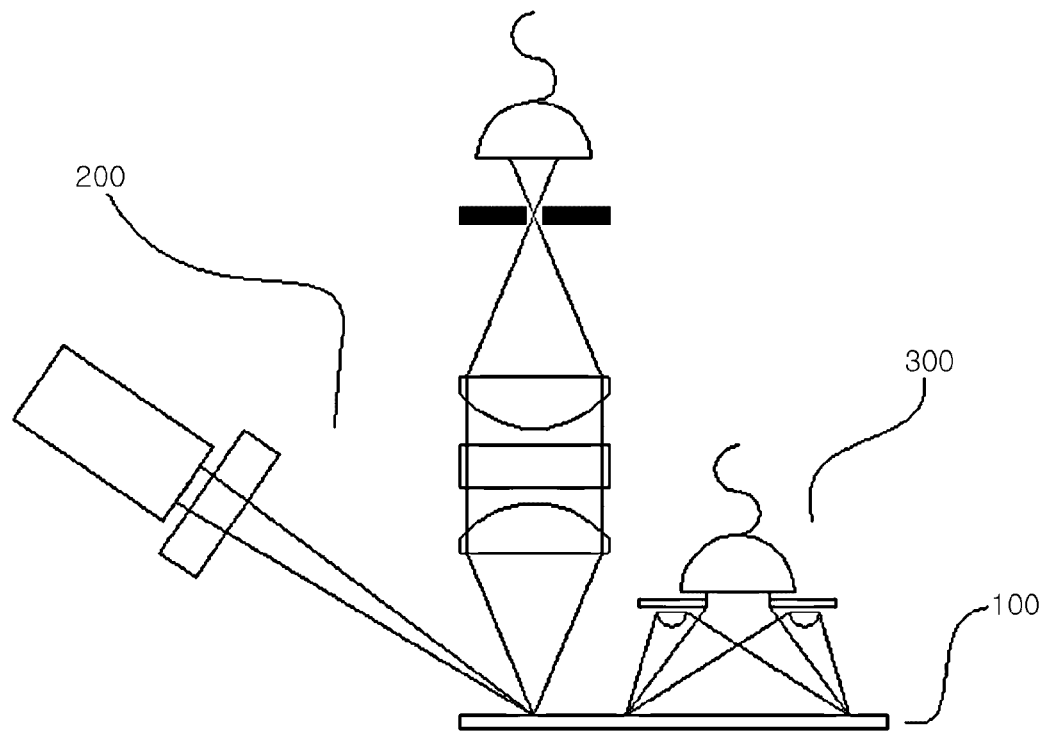
Integrated quantitative assay system for measurement of glycohemoglobin

[FIG. 3]
FIG. 3-A: Laser-induced epifluorescence detection device
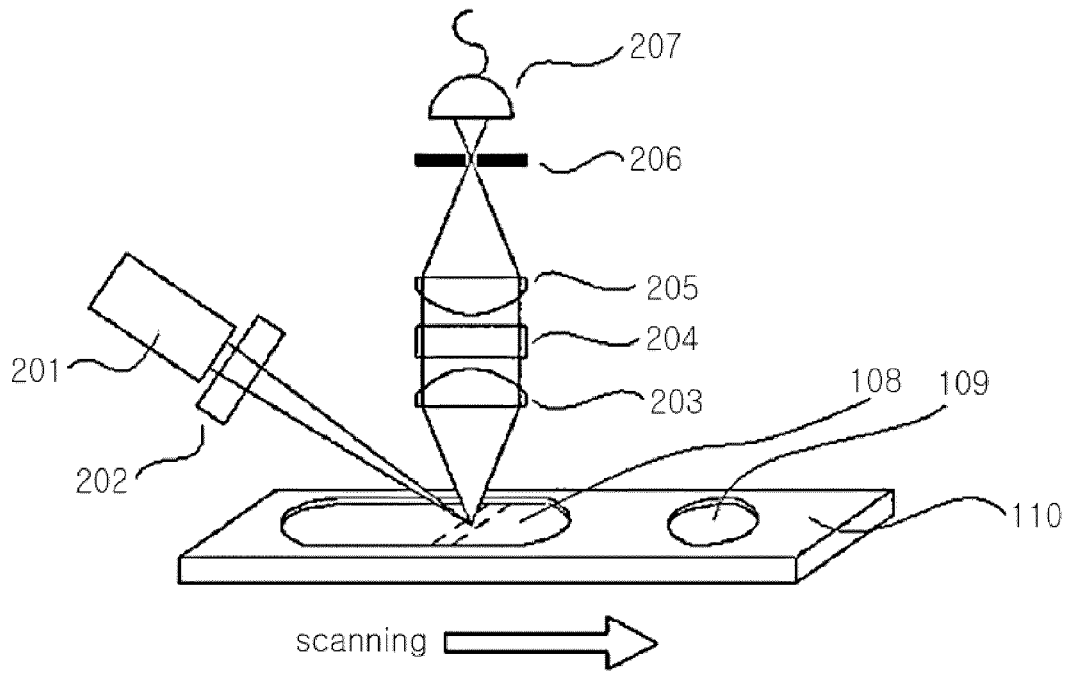
LED detection device
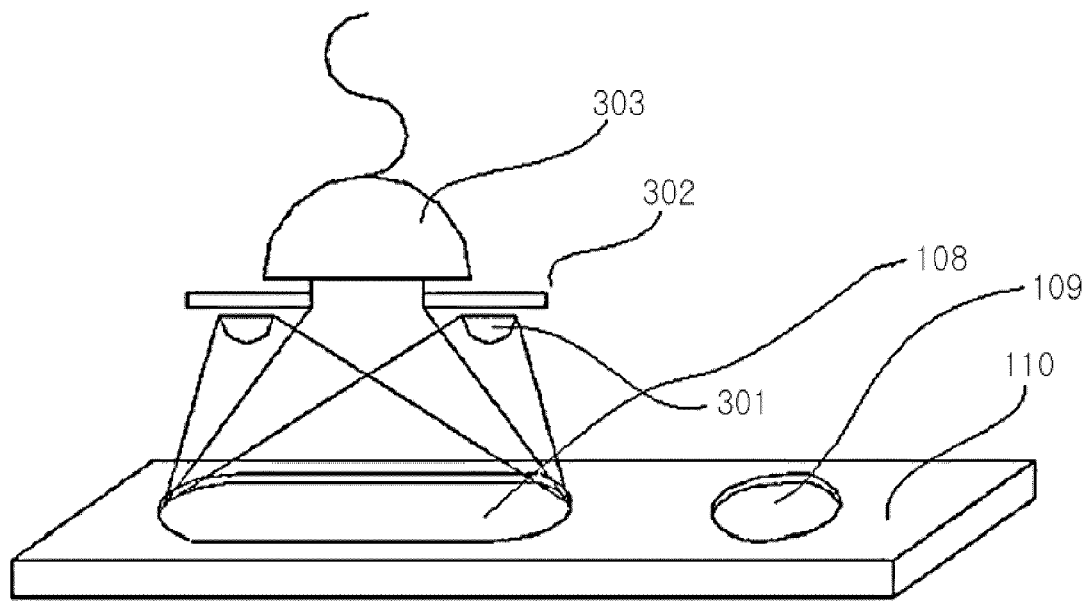
Measurement range and principle of detection device

[FIG. 4]
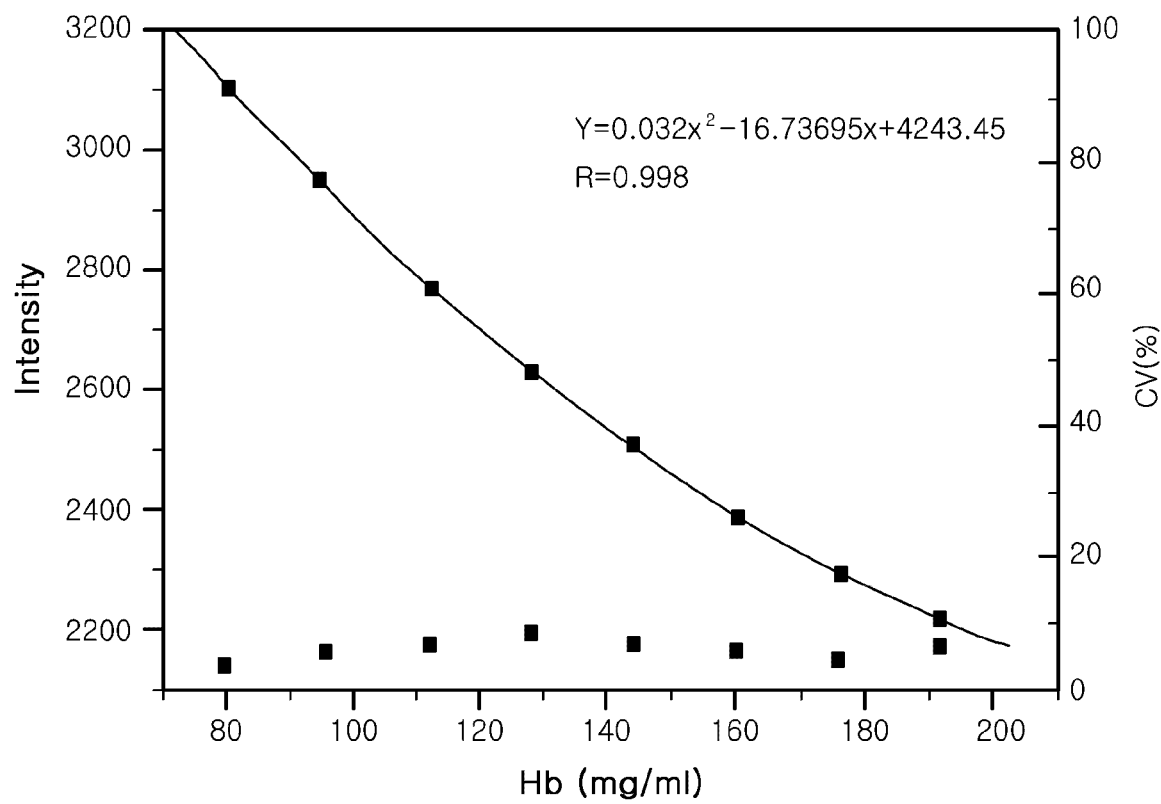
Hb standard curve using LED detection system

[FIG. 5]
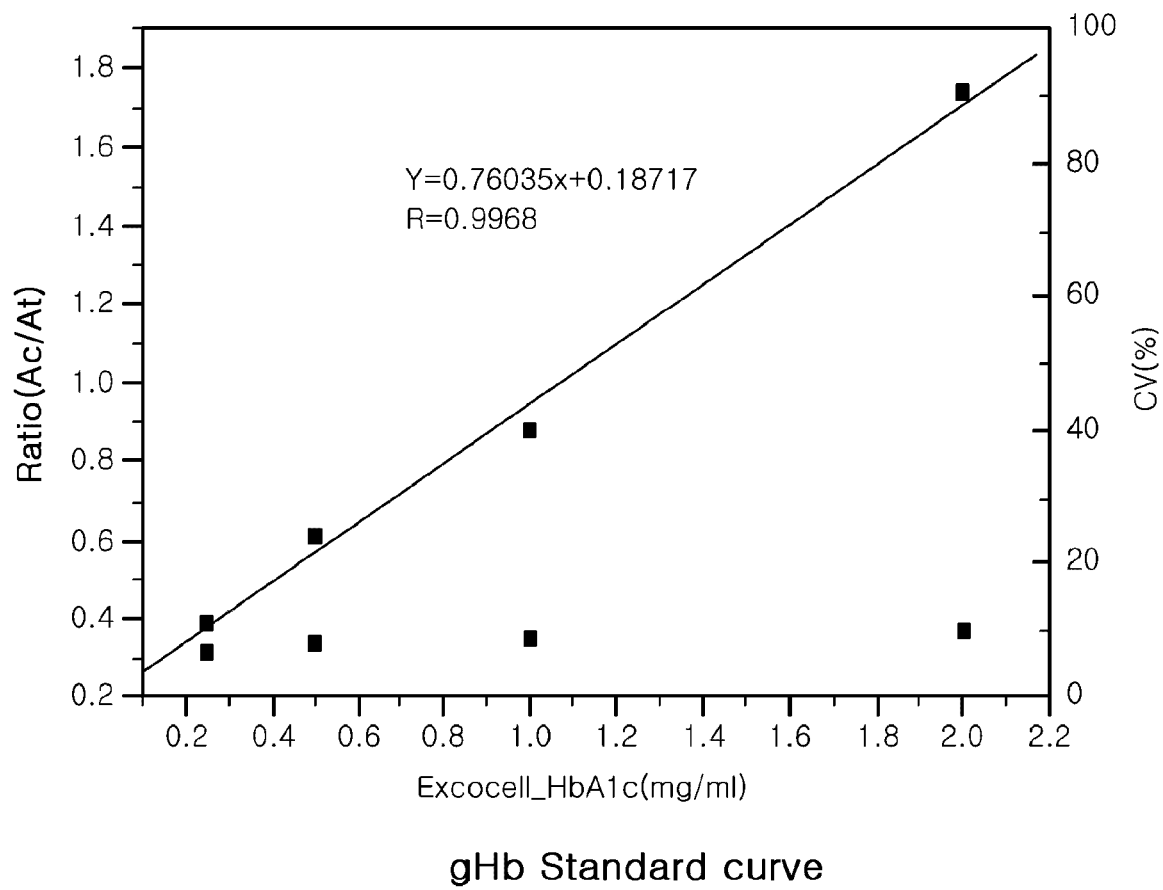
gHb Standard curve

[FIG. 6]
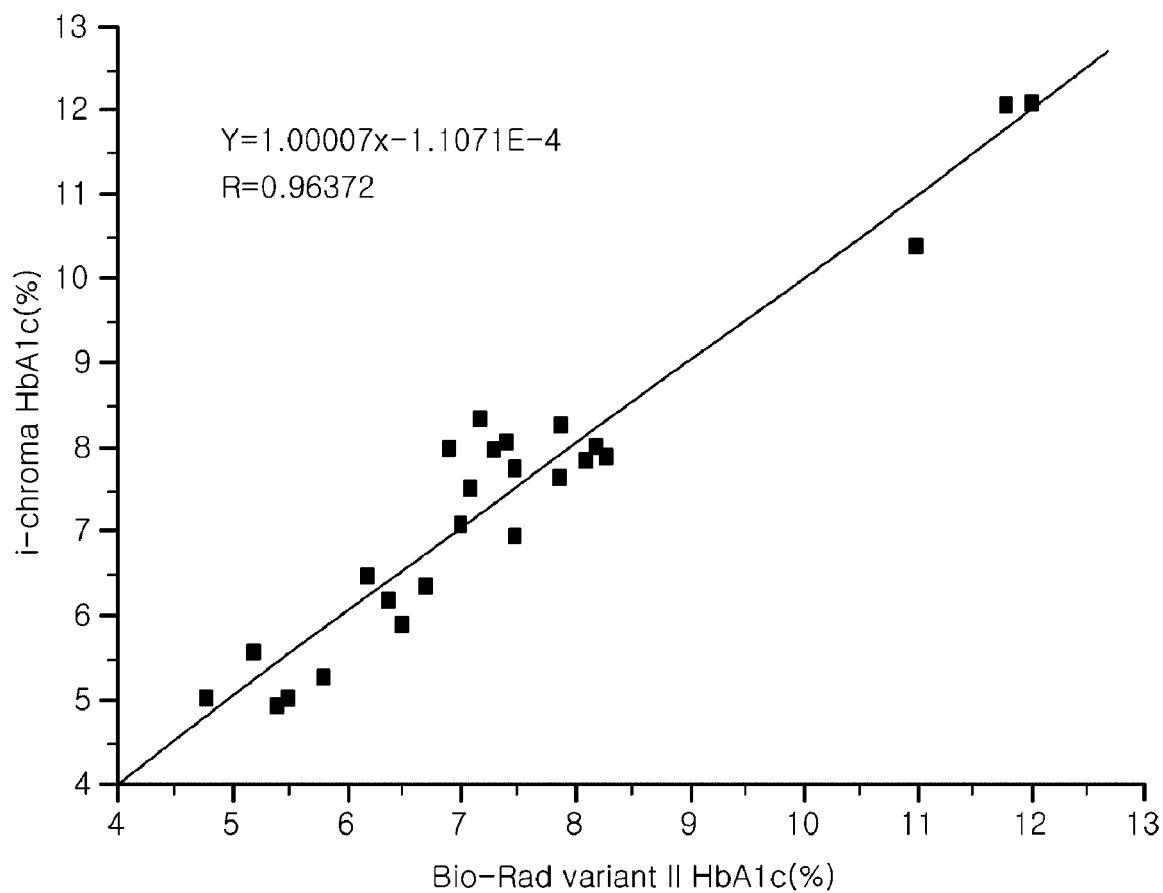
Comparison with Bio-Rad Variant II

SYSTEM FOR QUANTITATIVE MEASUREMENT OF GLYCOHEMOGLOBIN AND METHOD FOR MEASURING GLYCOHEMOGLOBIN

CROSS-REFERENCE TO RELATED APPLICATIONS

This application is an application under 35 U.S.C. §365(c) of International Application No. PCT/KR2008/006306, filed Oct. 24, 2008 designating the United States. The International Application No. PCT/KR2008/006306 was published in English as WO2009/099269 A1 on Aug. 13, 2009. This application incorporates herein by reference the International Application No. PCT/KR2008/006306 including the International Publication No. WO2009/099269 A1 in their entirety.

BACKGROUND

1. Field

The present invention relates to a lateral flow quantitative assay system capable of quantifying glycohemoglobin in blood with high sensitivity and a method thereof, in particular, an integrated quantitative assay method and system capable of simultaneously quantifying glycohemoglobin and total hemoglobin.

2. Description of the Related Art

Diabetes mellitus is a disease of abnormal carbohydrate metabolism in which glucose cannot enter the body's cells and be utilized by the body, and therefore remains in the blood in high concentrations to cause many complications. There are three types of diabetes mellitus: The major form of diabetes is type 1 diabetes, called insulin-dependent diabetes mellitus, which occurs when the beta cells of the pancreas are damaged by an autoimmune reaction and stop producing or secreting the hormone insulin. Type 2 diabetes, called non-insulin-dependent diabetes mellitus, is characterized by peripheral insulin resistance and impaired insulin secretion. The third type is gestational diabetes which occurs typically during pregnancy. It has been known that type 2 diabetes is the most prevalent, consisting of 90 to 95 percent of diabetes patients in advanced countries, while type 1 diabetes and gestational diabetes are less common.

Diabetes can be diagnosed by measuring urine or blood glucose levels, but urine glucose is not reliable for diagnosis. Blood glucose test is also inaccurate, since blood glucose levels can be affected by several factors, including diet and exercise. For these reasons, a glycohemoglobin test is a blood test used primarily to diagnose or monitor diabetes.

In 1986, the American Diabetes Association recommended glycohemoglobin testing twice a year to monitor all types of diabetes, and thus glycohemoglobin has gained acceptance as a stable index of blood glucose control, and has been commonly used to manage diabetes, since the DCCT (Diabetes. Control and Complications Trial) showed a direct relationship between glycohemoglobin level and diabetes complications in 1993.

Based on the results of the DCCT and UKPDS (United Kingdom Prospective Diabetes Study), current ADA (American Diabetes Association) guidelines recommend a goal glycohemoglobin of less than 7%. If the levels are greater than 8%, the ADA recommends that diabetes treatment be examined and modified as needed. In 2001, the American Association of Clinical Endocrinologists recommended a target glycohemoglobin of 6.5% or less, based on the UKPDS data that the incidence of diabetic retinopathy was shown to increase at the value of 6.5% or more. In 1999, the International Diabetes Federation (IDF) also recommended a target value of 6.5%.

In accordance with the clinical studies involving 1441 patients, conducted by the DCCT for 6.5 years, the risk of microvascular complications can be markedly reduced by achieving tight blood glucose control. Therefore, it is essential that patients or physicians consider strict management of glucose levels.

Human adult hemoglobin typically consists of three types of Hb; 97% HbA, 2.5% HbA2 and 0.5% HbF. Among them, HbA consists of four polypeptide chains—two alpha chains, each containing 141 amino acids, and two beta chains, each containing 146 amino acids. Chromatographic analysis of HbA identifies 96% major Hb and 5~6% minor Hb, termed HbA1 or glycohemoglobin. The glycated form, formed by attachment of glucose to the N-terminal valine of the beta chain, accounts for 80% of HbA1, and HbA1$a$ and HbA1$b$ accounts for the remaining portion.

Glycation is the non-enzymatic addition of a sugar molecule to amino groups of proteins, and is a very slow and irreversible reaction. Glycohemoglobin is formed continuously by the addition of blood glucose to hemoglobin, and the proportion of glycohemoglobin to hemoglobin is dependent upon the exposure time of erythrocyte to glucose. Specifically, during glycation, glucose is attached to the valine residue of HbA to form a HbA1c precursor, which subsequently undergoes Amadori rearrangement to form a stable ketoamide form. At this time, the increase in blood glucose levels increases the exposure time of hemoglobin to circulating glucose, resulting in the high proportion of glycohemoglobin. Thus, the percentage of glycohemoglobin reflects the blood glucose levels. In addition, the glycohemoglobin test can help monitor the long-term control of blood glucose levels, since the life span of erythrocytes ranges from 60 to 120 days.

Various methods for the determination of glycohemoglobin in blood have been developed. Currently available methods include ion exchange chromatography, affinity chromatography, electrophoresis, combined colorimetry or the like. These methods are difficult to practice, and thus require advanced skills and equipment. In addition, concerning the development trends of disposable clinical analysis systems, there have been proposed very useful quantitative assay systems for use at a remote site, at home, or point-of-care testing, such as visual, optical, and electrochemical detection methods.

Recently, monoclonal and polyclonal antibodies that recognize the N-terminal peptide residues of glycohemoglobin have been developed (U.S. Pat. No. 4,647,654), and thus many studies have been advanced on quantitative immunoassay systems for glycohemoglobin using the antibodies. Since antibodies recognizing glycohemoglobin are used in the immunoassay systems, they are advantageous in terms of specificity and sensitivity. When glycohemoglobin levels are determined by immunoassay, it is essential to prepare antibodies capable of recognizing a specific glycosylated region of glycohemoglobin with high sensitivity. Since the glycosylated region of glycohemoglobin in blood is not externally exposed, glycohemoglobin has to be first modified in order to be recognized by the antibodies. Subsequently, hemoglobin has to be converted into methemoglobin for spectroscopic measurement of total hemoglobin. Methemoglobin has a property of absorbing light at a specific wavelength, and thus its absorbance is measured by a spectroscopic method to quantify total hemoglobin concentration. In addition, modified glycohemoglobin is measured by an immunological method to quantify the amount of glycohemoglobin in blood.

Immunoassay devices are divided into flow-through type and lateral flow type according to their principle. In the flow-through type, an antibody is covalently coupled to the surface of a porous matrix, and an analyte in a sample binds with the immobilized antibody. Subsequently, a secondary capture antibody is added thereto, followed by visual detection with chromogenic enzyme substrates. There are two types of lateral flow immunoassay devices; one type is an all-in one device, and the other type is a device, in which a fluid sample binds with a labeled antibody, while passing through a labeled antibody-immobilized porous matrix.

The lateral flow type has a structure comprising a sample pad, to which a sample is applied, a releasing pad coated with a detector antibody, a developing membrane or strip, through which components of the sample move to be individually separated and to undergo antibody-antigen reaction, and an absorption pad which is provided to continuously absorb fluid so as to cause the sample to continue moving through the device. The lateral flow assay can be widely and conveniently used in various fields such as pregnancy diagnosis, cancer diagnosis, and microbe detection. However, since quantification cannot be performed with the naked eye and hence, an exact amount of an analyte cannot be determined, its application is restricted.

Immunoassay using antibodies against HbA1c generally use a principle of determining the change of turbidity of a reaction system. In this regard, since the HbA1c-specific epitope only occurs once at the N-terminus of a beta chain of the glycohemoglobin, there is no aggregation of the antigen-antibody complex. Therefore, a polyhapten having several epitopes is reacted with an antibody to form an insoluble immune complex. This can be measured turbidimetrically. The turbidimetric signal is inversely proportional to the concentration of glycohemoglobin in the sample. However, this method is disadvantageous in that a specialized analytical laboratory and automated equipment are required, since it comprises several processing steps.

Korean Patent Publication No. 2004-0018893 discloses a glycohemoglobin test kit, which consists of a buffer solution containing antibodies against glycohemoglobin, a strip containing antibodies against hemoglobin, and a washing solution. Unfortunately, an exact amount of glycohemoglobin cannot be determined, since the kit is a semiquantitative assay system, in which a dye is added to the antibodies against glycohemoglobin, and color change caused by the presence of HbA1c is detected by the naked eye or by visual comparison against a color chart.

The RIA or ELISA method which can quantify an analyte at present involves several complicated steps for such quantification, including treatment with an enzyme and washing. Therefore, there is a great demand for a general assay method which can perform quantification more rapidly, conveniently and sensitively.

SUMMARY

One aspect of the invention provides an assay device comprising a pad configured to receive a sample and a detector for providing a mixture comprising the sample and the detector, the sample comprising glycohemoglobin and non-glycohemoglobin, the detector having specificity in binding with glycohemoglobin while having little specificity in binding with non-glycohemoglobin, wherein the detector is included in the mixture in a predetermined amount that is more than sufficient to bind with substantially all glycohemoglobin; a strip comprising a chromatographic medium configured to receive the mixture from the pad and to let the mixture migrate in a direction in the chromatographic medium; a first detection zone provided in the strip and distanced at a first predetermined distance from the pad in the direction, wherein the first detection zone comprises a captor having specificity in binding with the detector, wherein the captor is immobilized in the first detection zone and provided in an amount that is sufficient to capture substantially all the detector that are not bound with glycohemoglobin and reach the first detection zone, wherein the first detection zone provides an access for detecting an amount of the detector captured in the first detection zone; and a second detection zone provided in the strip and distanced at a second predetermined distance from the pad in the direction, wherein the second detection zone provides an access for detecting an amount of non-glycohemoglobin and glycohemoglobin that are staying or passing in the second detection zone at a detection time. The foregoing detector may further comprise a fluorescent moiety, wherein the access of the first detection zone is configured to make available detection of fluorescence of the fluorescent moiety in response to first light beams irradiated to the first detection zone. The access of the second detection zone in the device may be configured to make available detection of light emitted from non-glycohemoglobin and glycohemoglobin in response to second light beams irradiated to the second detection zone.

In the foregoing device, the pad may be configured to receive the sample and the detector in a pre-mixed form. The pad may comprise a sample receiving portion for receiving the sample and a detector receiving portion for receiving the detector, wherein the pad is further configured to mix the received sample and detector therein. The detector may comprise a glycohemoglobin -binding site that is specific in binding with glycohemoglobin, wherein the captor has specificity in binding with the glycohemoglobin -binding site of the detector.

According to some embodiments of the invention, the first detection zone may extend in a first length from the first distance in the direction, and the second detection zone may extend in a second length from the second distance in the direction. The first detection zone and the second detection zone may at least partly overlap with each other. Alternatively, the first detection zone and the second detection zone may not overlap with each other. Another aspect of the invention provides an assay system comprising the foregoing device; a first detection device configured to irradiate first light beams to the first detection zone and to detect fluorescence from a fluorescent moiety bound to a detector in response to the first light beams; and a second detection device configured to irradiate second light beams to the second detection zone and to detect light emitted from non-glycohemoglobin and glycohemoglobin in response to the second light beams. The first and second detection devices of the device may be arranged and configured relative to each other such that the first detection device irradiates the first light beams to the first detection zone and that simultaneously or sequentially the second detection device irradiates the second light beams to the second detection zone without having to move the assay device relative to one of the first and second detection devices. The first detection device may comprise a first light source and a first sensor, which are integrated in a single piece or provided in separate pieces, and wherein the second detection device comprises a second light source and a second sensor, which are integrated in a single piece or provided in separate pieces. Still another aspect of the invention provides an assay method comprising providing the foregoing device; providing, in the pad, a mixture comprising glycohemoglobin in an unknown amount, non-glycohemoglobin in an unknown amount and a detector in a predetermined amount, the detector having specificity in binding with glycohemoglobin while having little specificity in binding with non-glycohemoglobin, wherein the detector is included in the mixture in a predetermined amount that is more than sufficient to bind with substantially all glycohemoglobin in the mixture; permitting the mixture to migrate in the chromatographic medium of the strip in the direction away from the pad, wherein substantially all the detector that are not bound with glycohemoglobin are captured in the first detection zone upon reaching the first detection zone, wherein some of non-glycohemoglobin and glycohemoglobin reach the second detection zone; measuring an amount of the detector captured in the first detection zone; and measuring an amount of the non-glycohemoglobin and glycohemoglobin that are staying or passing in the second detection zone at a detection time, which is past a period after initial migration of the mixture in the strip. In one embodiment, the foregoing method may further comprise computing the unknown amount of glycohemoglobin contained in the mixture using the measured amount of the detector captured in the first detection zone and further using the predetermined amount of the detector. In another embodiment, the foregoing method may further comprise determining a total amount of glycohemoglobin and non-glycohemoglobin contained in the mixture using the measured amount of the non-glycohemoglobin and glycohemoglobin in the second detection zone and further using reference data of migration of non-glycohemoglobin and glycohemoglobin in the chromatographic medium. In still another embodiment, the foregoing method may further comprise computing the unknown amount of glycohemoglobin contained in the mixture using the measured amount of the detector captured in the first detection zone and further using the predetermined amount of the detector; computing a total amount of glycohemoglobin and non-glycohemoglobin contained in the mixture using the measured amount of the non-glycohemoglobin and glycohemoglobin in the second detection zone; and computing a ratio of the computed amount of glycohemoglobin and the computed total amount of glycohemoglobin and non-glycohemoglobin contained in the mixture.

In the foregoing method, the detector may further comprise a fluorescent moiety, wherein measuring an amount of the detector may comprise: irradiating first light beams to the first detection zone; and detecting fluorescence of the fluorescent moiety in response to the first light beams. In some embodiments, measuring an amount of the non-glycohemoglobin and glycohemoglobin may comprise: irradiating second light beams to the second detection zone; and detecting light emitted from non-glycohemoglobin and glycohemoglobin in response to the second light beams at the detection time. In some other embodiments, measuring an amount of the detector may comprise using a first detection device comprising a first light source and a first sensor, wherein measuring an amount of the non-glycohemoglobin and glycohemoglobin may comprise using a second detection device comprising a second light source and a second detector, wherein the first and second detection devices may be arranged and configured relative to each other such that the first detection device may irradiate the first light beams to the first detection zone and that simultaneously or sequentially the second detection device may irradiate the second light beams to the second detection zone without having to move the assay device relative to one of the first and second detection devices. The detector may comprise a glycohemoglobin-binding site that is specific in binding with glycohemoglobin, wherein the captor has specificity in binding with the glycohemoglobin-binding site of the detector.

BRIEF DESCRIPTION OF DRAWINGS

FIG. 1 is a perspective view showing the integrated quantitative assay system for quantifying the blood hemoglobin levels according to the present invention;

FIG. 2 is a perspective view showing the lateral flow quantitative assay strip according to the present invention;

FIG. 3A is a perspective view showing the optical system for measuring glycohemoglobin using the laser-induced epifluorescence detection device, and FIG. 3B is a perspective view showing the optical system for measuring total hemoglobin using LED;

FIG. 4 is a hemoglobin standard curve using the LED detection device;

FIG. 5 is a glycohemoglobin standard curve; and

FIG. 6 is a graph showing the results of comparing performance between the known large-sized equipment and the quantitative assay system according to the present invention.

EXPLANATION OF NUMERALS

100: Lateral flow quantitative assay strip
101: Backing card
102: Sample pad
103: Conjugate releasing pad
104: Chromatography medium
105: Absorption pad
106: Antigen analyte-detection zone
107: Pigment analyte-detection zone
108: Window
109: Sample holder
110: Strip housing
200: Laser-induced epifluorescence detection device
201: Laser
202: Shape control lens for laser beam
203: Collecting lens
204: Fluorescent filter
205: Condenser lens
206: Spatial filter
207: Optical detector
300: LED detection device
301: LED light source
302: Aperture
303: Photo detector

DETAILED DESCRIPTION OF EMBODIMENTS

As mentioned above, the conventional assay devices, which quantify the amount of glycohemoglobin using antibodies, have a low sensitivity, and the immunoassay involves several complicated steps for such quantification, including treatment with an enzyme and washing. Accordingly, the present inventors have made an effort to provide an integrated quantitative assay system capable of quantifying glycohemoglobin and total hemoglobin at the same time, and a method which can perform quantification more rapidly, conveniently and sensitively, thereby completing the present invention.

Considering the advantages of immunoassay and needs for quantitative analysis, the present inventors have developed a point-of-care device for measuring glycohemoglobin levels, thereby simply quantifying the blood glycohemoglobin levels to achieve early diagnosis of diabetes. Accordingly, one aspect of the present invention is to provide a method for preventing or minimizing the risk of complications in patients with diabetes, and to provide convenience for patients or physicians to keep strict management of glucose levels.

In one embodiment, the present invention may provide an integrated quantitative assay system capable of quantifying glycohemoglobin and total hemoglobin at the same time, namely, an integrated quantitative assay system comprising a lateral flow assay strip capable of quantifying glycohemoglobin, a laser-induced epifluorescence detection device for quantifying an antigen analyte, and an LED detection device for quantifying a pigment analyte.

In another embodiment, the present invention may provide a method for quantifying the antigen analyte in a sample using specificity and selectivity of immune responses, in which while the sample containing the antigen analyte and a predetermined amount of detector move along the lateral flow assay strip, and competitive antigen-antibody reaction occurs between the detector in the sample and a captor immobilized on medium, signals generated by the labeled detector are measured, and the amount of pigment analyte on the lateral flow assay strip is separately measured to calculate the proportion of antigen analyte to pigment analyte.

As described above, an integrated quantitative assay system consisting of a lateral flow assay strip, a laser-induced epifluorescence detection device, and an LED detection device is to provide a method for effectively quantifying glycohemoglobin by antigen-antibody reaction, thereby being very useful for patients in need of strict management of glucose levels.

In accordance with a first aspect, the present invention provides a lateral flow quantitative assay strip comprising a backing card, a sample pad, a chromatography medium, and an absorption pad, in which the backing card supports all of the components in the strip, and the sample pad and the absorption pad are adhered to each end of the backing card without overlapping each other; the sample pad at the end of direction adhered to absorption pad overlaps with one end of the chromatography medium, to which a sample is first applied; the other end of the chromatography medium overlaps with the absorption pad, and a captor is immobilized on the chromatography medium with a predetermined distance from the sample pad. Preferably, the strip may further include a conjugate releasing pad, on which a fluorescently-labeled detector is adsorbed, between the sample pad and the chromatography medium. More preferably, the strip may further include a strip housing that covers the whole strip except the sample application site, the epifluorescence detection zone, and the LED detection zone in order to prevent contamination of the strip.

The term "fluid sample" or "sample", as used herein, refers to a compound of composition to be analyzed, which contains an analyte or a detector and an analyte, and the fluid sample or sample to be used in the present invention refers to a liquid phase material or a liquid-like fluid material that is able to migrate through the chromatography medium.

The term "analyte", as used herein, refers to a compound to be analyzed, contained in a sample, and encompasses antigen analyte and pigment analyte. In addition, the term "pigment analyte" and "antigen analyte", as used herein, refer to a protein and a glycosylated protein, respectively, in particular, hemoglobin and glycohemoglobin. The antigen analyte is involved in antigen-antibody reaction, and both of the pigment analyte and antigen analyte generate signals by LED according to the present invention.

The term "detector", as used herein, refers to antibodies against the above mentioned antigen analyte, preferably antibodies against glycohemoglobin, and more preferably those labeled with fluorescent materials.

The term "captor", as used herein, refers to a material or compound being identical to the antigen analyte in a sample, or a material containing a structure being identical to the detector-recognizing region of the antigen analyte, a glycosylated protein, preferably human glycohemoglobin. The captor is, immobilized on the strip, specifically and selectively able to capture free detector in the mixture that moves along the strip.

The term "epifluorescence", as used herein, refers to the fluorescence emitted from a conjugate of fluorescently-labeled detector-analyte or fluorescently-labeled detector, which are fixed in the antigen analyte-detection zone(first detection zone), of the lateral flow assay strip by chromatography.

The term "adsorption", as used herein, means that a concentrated material is adhered to the chromatography medium or the pad that constitutes the strip. It may migrate along the mobile phase of chromatography, but may be immobilized by a suitable treatment.

The term "immobilization" or "immobilized", as used herein, means that a compound is held on the chromatography medium or the strip, and especially refers to a state in which the compound is not solubilized in the mobile phase of chromatography or a solvent, and does not migrate along with the mobile phase but is fixed in place.

In accordance with another aspect, the present invention provides an integrated lateral flow quantitative assay system capable of simultaneously quantifying amounts of antigen analyte and pigment analyte in the sample, comprising the lateral flow assay strip in accordance with the first aspect, a laser-induced epifluorescence detection device that determines the amount of antigen analyte by measuring epifluorescence of the fluorescent material on the lateral flow assay strip, and an LED (light emitting diode) detection device that determines the amount of pigment analyte on the lateral flow assay strip.

In the first detection device, specifically, in the epifluorescence detection device, light passed through the shape control lens for laser beam and the exciter filter is illuminated, and the reflected light passes through a collection lens to form parallel light. The parallel light passes through a fluorescent filter to remove scattered light, and subsequently, pure fluorescence components enter a condenser lens. By the condenser lens, the pure fluorescence components are focused to a center of a spatial filter. In the spatial filter, light except for the pure fluorescence components is removed. The light enters an optical detector. A digital signal converted by an analog digital converter (ADC) connected to the optical detector is transmitted to a central processing unit (CPU), and the amount of the analyte is determined as a relative value by comparing fluorescence intensity of the conjugate with reference fluorescence intensity.

In the second detection device, specifically in the LED detection device, the amount of the pigment analyte is determined, based on the principle that the amount of light either absorbed or scattered by the LED light source varies depending on the amount of pigment analyte. In particular, the analyte is illuminated by the LED light source, and light scattered by the analyte is filtered by the spatial filter positioned in front of the optical axis. The light scattered by the pigment analyte is only provided to the optical detector. The light signals detected by the optical detector are transmitted to CPU via ADC, so as to determine the amount of the pigment analyte in the sample.

In accordance with still another aspect, the present invention provides a method for measuring blood glycohemoglobin levels using the integrated lateral flow quantitative assay system according to the present invention.

Specifically, a sample which is expected to contain antigen analyte and pigment analyte is applied onto the sample pad of the lateral flow assay strip, and the fluid sample moves through the chromatography medium, such that a conjugate of detector-antigen analyte is formed due to a primary immune response by adding a predetermined amount of detector to the sample before application or during migration. As the sample develops along the chromatography medium, a secondary immune response competitively occurs between the captor, immobilized on the chromatography medium that is located at a predetermined distance from the sample pad, and the detector-antigen analyte conjugate, and/or the free detector, so as to form a conjugate. After the competitive reaction, the amount of detector that binds to the captor immobilized on the chromatography medium and the amount of pigment analyte on the chromatography medium are separately measured, and then the proportion of antigen analyte to the analyte in the sample is calculated to quantify the antigen analyte.

Preferably, the predetermined amount of detector is labeled with a fluorescent material, and the detector is mixed with the liquid sample, before applying the sample to the strip. Alternatively, if the lateral flow assay strip includes a conjugate releasing pad, the detector is adsorbed onto the conjugate releasing pad in advance. While the applied sample migrates along the chromatography medium, and passes through the conjugate releasing pad, the detector is solubilized in and/or mixed with the liquid sample. Subsequently, the detector binds with the antigen analyte in the sample to form a fluorescently-labeled detector-antigen analyte conjugate. In the absence or lack of the antigen analyte, the detector migrates along the chromatography medium in a free form.

The captor is immobilized, at a predetermined distance (hereinbelow, referred as "antigen analyte-detection zone") from the sample application site, on the chromatography medium. When the sample reaches to the area where the captor is immobilized, the captor binds with the free detector and/or the detector-antigen analyte conjugate to form a detector-captor conjugate. Finally, the laser-induced epifluorescence detection device capable of detecting the fluorescently-labeled detector collects signals generated from the antigen analyte-detection zone, so as to determine the amount of antigen analyte, namely, the amount of glycohemoglobin conjugated with the detector.

Meanwhile, the amounts of hemoglobin and glycohemoglobin on the chromatography medium are determined by LED capable of detecting the pigment analyte. The proportion of antigen analyte to the pigment analyte is calculated to quantify the amount of the antigen analyte in the sample.

Hereinafter, the integrated lateral flow quantitative assay system consisting of the lateral flow assay strip, the laser-induced epifluorescence detection device, and the LED detection device, and a method for simultaneously quantifying the amounts of total hemoglobin and glycohemoglobin in blood using the same will be described in detail with reference to the Drawings.

FIG. 1 is a perspective view showing the lateral flow assay strip according to the preferred Example of the present invention, in which the strip comprises a backing card 101, a sample pad 102, a conjugate releasing pad 103, a chromatography medium 104, and an absorption pad 105. Each component constituting the lateral flow assay strip will be described in detail, below.

Backing Card

The backing card 101 supports all of the components in the strip, and the chromatography medium 104 may be the backing card per se, when it is omitted. The backing card is typically made of water-insoluble, non-porous and rigid material and has a length and width equal to the pads situated thereon, along which the sample develops, but may have a dimension being less or greater than the pad. In preparation of the backing card, various natural and synthetic organic and inorganic materials can be used, provided that the backing card prepared from the material should not hinder capillary actions of the absorption material, nor non-specifically bind to an analyte, nor interfere with the reaction of the analyte with a detector. Representative examples of polymers usable in the present invention include, but are not limited to, polyethylene, polyester, polypropylene, poly (4-methylbutene), polystyrene, polymethacrylate, poly(ethylene terephthalate), nylon, poly(vinyl butyrate), glass, ceramic, metal and the like.

On the backing card, a variety of pads are adhered by means of adhesives. Proper selection of adhesives may improve the performance of the strip and lengthen the shelf life of the strip. According to the present invention, pressure-sensitive adhesives (PSA) may be representatively used in the lateral flow assay strip. Typically, the adhesion of different pads of the lateral flow assay strip is accomplished as the adhesive penetrates into pores of the pads, thereby binding pads together with the backing card. With respect to such binding, ability of an adhesive to flow under normal conditions is referred to as "cold flow". Since no heat is applied when coating PSA onto the pad, cold flow of a certain level is indispensable for binding between the pad and the backing. If the level of cold flow is too low, the adhesive migrates to the pads with which it is bound during storage of the strip, thereby clogging the pores, forming hydrophobic stains or leading to problems of redamping the pad. Such problems associated with the cold flow of the adhesive can be solved by using a direct-casting membrane. For example, in the direct-casting membrane, a supporting plastic sheet prevents the adhesive from entering pores of the membrane and thus vertical migration of the adhesive is prevented during storage.

Sample Pad

The sample pad 102 is located at one end of the strip, and one end of the sample pad overlaps with the chromatography medium 104 or a part of conjugate releasing pad 103 when a conjugate releasing pad 103 is additionally included.

The sample pad basically acts to receive the fluid sample containing an analyte. Other than this function, the sample pad may have a function to filter insoluble particles in the sample. From this point of view, preferred sample pads of the present invention are composed of cellulose filter paper or glass fiber filter paper capable of providing the filtering function. Usually, a cellulose membrane (grade 903) produced by S & S is used.

Preferably, the sample pad is treated in advance to prevent the analyte in the sample from being non-specifically adsorbed thereto, to allow the components of the sample to readily migrate through the chromatography medium, to maintain the sensitivity of the reaction and to prevent undesirable nonspecific reactions which may occur between the fluorescently-labeled detector and components of the sample. The pretreatment of the sample pad is generally performed by treating the pad with an inactive protein or surfactant. For instance, the pretreatment with inactive protein may be carried out by immersing the pad material in a solution of 0.1% to 10% skim milk powder in 0.1 M Tris buffer solution(pH 6 to 9) comprising 0.1 to 10% BAS(Bovine Serum Albumin) and/or 0.1 to 10% casein solution. The pretreatment with a surfactant may be carried out by immersing the pad in Triton X-100 or Tween 20. However, these pretreatment steps are determined in accordance with kinds of analytes and samples.

Conjugate Releasing Pad

The lateral flow assay strip may selectively include a conjugate releasing pad 103. In this regard, the conjugate releasing pad is adhered to the backing card 101 such that one end of the conjugate releasing pad overlaps with the sample pad 102, and the other end of the conjugate releasing pad overlaps with the chromatography medium 104.

On the conjugate releasing pad, a fluorescently-labeled detector capable of reacting with an analyte in the sample to form a conjugate is adhered but is not immobilized. Upon forming a conjugate via reaction with an analyte in the sample, it can move together with the sample through the chromatography medium.

Methods for attaching a reagent onto the conjugate releasing pad may include the known methods previously performed. Specific examples thereof include an impregnation, drying, or freeze-drying process, but are not limited thereto.

It is preferred for material of the conjugate releasing pad to have a rapid filtering speed and a good ability to adhere particles. As such material, synthetic material such as polyester and glass fiber filter can be used. Commonly, glass fiber of a main ingredient in glass and polyester may be used, and the glass fiber produced by S & S was used in the present Examples. Since these are biologically inactive and have more delicate fibrous material than natural material, they are not distorted or swollen when an aqueous reagent or sample is applied. Preferably, the conjugate releasing pad is pretreated with a reagent such as a surfactant, so that an analyte is prevented from non-specifically binding to the fluorescently-labeled detector on the releasing pad and the conjugate can smoothly be released and migrate.

The conjugate releasing pad may be treated with a stabilizing agent and shielding agent in order to improve its performance and stability. Examples of the stabilizing agent may include saccharides such as sucrose and trehalose. Examples of the shielding agent may include proteins such as BSA (Bovine Serum Albumin), gelatin, casein, and skim milk, but are not limited thereto.

Chromatography Medium

Each end of the chromatography medium 104 is overlapped by the sample pad 102 and the absorption pad 105. When the conjugate releasing pad is additionally included, the conjugate releasing pad 103 and the absorption pad 105 are disposed without overlapping each other.

The chromatography medium may be adhered to the backing card 101. Alternatively, the chromatography medium may be the backing card per se.

The material of the chromatography medium may be any one that can allow the fluid sample and analyte to rapidly move via capillary action to reach the captor immobilized thereon and preferably has homogeneous properties. Typically, the chromatography medium refers to a porous material having a pore diameter of at least $0.1\mu$, preferably $1.0\mu$ and through which an aqueous medium can readily move via capillary action. Such material generally may be hydrophilic or hydrophobic, including for example, inorganic powders (e.g., fiber containing papers, such as filter paper and chromatographic paper), synthetic or modified naturally occurring polymers (e.g., nitrocellulose, cellulose acetate, poly (vinyl chloride), polyacrylamide, cross-linked dextran, agarose, polyacrylate), and either used by themselves or in conjunction with other materials. Also, ceramics may be used.

The chromatography medium may be multifunctional or be modified to be multifunctional to covalently bind to the captor.

Examples of the chromatography medium having the above properties include AE98, AE99, and AE100 that are produced by S&S, HF090, HF120, HF135, HF180, and HF240 that are produced by Millipore, and CN90, CN140, and CN200 that are produced by Sartorius. Preferred chromatography medium is CN90 membrane (produced by Sartorius). Since the CN90 membrane has the smallest variation ($\pm 3$ sec) in flow rate, it has good reproducibility. It is sufficient that its binding capacity capable of binding ligands per unit area ($cm^2$) is 10 to 30 ug, since amplification of fluorescent substances is excellent.

On the chromatography medium, antibody or HbA1c antigen is added as a captor on a specific zone (antigen analyte-detection zone) in order to measure glycohemoglobin levels, and thus fluorescent signals generated from the zone are measured by a laser-induced epifluorescence detection device, thereby quantifying glycohemoglobin levels.

Absorption Pad

The absorption pad 105 is located farthest from the end of the sample pad in the lateral flow assay strip, and is overlapped by the end of the chromatography medium.

The absorption pad is a means for physically absorbing the sample which has chromatographically moved through the chromatography medium via capillary action and for removing unreacted substances. Thus, the absorption pad is located at the end of the lateral flow assay strip to control and promote movement of samples and reagents and acts as a pump and container for accommodating them. The speeds of samples and reagents may vary depending on the quality and size of the absorption pad. Commonly used absorption pads are formed of water-absorbing material such as cellulose filter paper, non-woven fabric, cloth, and cellulose acetate.

FIG. 2 shows the integrated quantitative assay system according to the present invention. The integrated quantitative assay system according to the present invention includes the above described lateral flow assay strip 100, a laser-induced epifluorescence detection device 200, an LED detection device 300, and a drive. In addition, FIGS. 3-A and 3-B show the laser-induced epifluorescence detection device 200 and the LED detection device 300, which are used in the integrated quantitative assay system according to the present invention. Hereinafter, the laser-induced epifluorescence detection device and the LED detection device that constitute the integrated quantitative assay system will be described in detail.

Laser-induced Epifluorescence Detection Device

The laser-induced epifluorescence detection device (FIG. 3-A) includes a laser 201, a shape control lens for laser beam 202, an exciter filter, a collection lens 203, a fluorescent filter 204, a condenser lens 205, a spatial filter 206, an optical detector 207, an analog digital converter (ADC), and a CPU. The laser-induced epifluorescence detection device may be the same as used in Korean Patent No. 10-0639776 which was applied by the present inventor. The laser-induced epifluorescence detection device is operated as follows. Light emitted from a laser light source is processed into a point of light or a linear shape, passes through an excitation filter, and is illuminated to a predetermined position of a sample. A fluorescent substance attached to a target material placed in the position emits fluorescence. The fluorescence passes through a collecting lens, fluorescent filter, and condenser lens, and the fluorescence components are focused to a center of a spatial filter. The parallel light enters an optical detector. A digital signal is converted by an analog digital converter (ADC) and a central processing unit (CPU), and printed out.

The laser-induced epifluorescence detection device is used for the quantification of antigen analyte, preferably glycohemoglobin levels in blood. Light emitted from a laser light source is illuminated to the fluorescently-labeled detector which specifically bonds with an antigen analyte. The emitted fluorescence is collected by the optical system, and quantified in the optical detector. That is, when immune responses are terminated after applying the fluid sample, the strip is moved by the drive at a predetermined speed in the direction of light source. During scanning process, the laser-induced fluorescence is measured by the detector. Preferably, while the strip moves, signals generated in the antigen analyte-detection zone are collected several times and quantified.

LED Detection Device

In the present invention, the LED detection device (FIG. 3-B) is used in order to optically measure a total amount of hemoglobin in the analyte. Unlike fluorescent materials involved in immune responses, hemoglobin and glycohemoglobin are intrinsically red-colored, and thus green-LED is used as a light source. That is, the needed light source is a green-LED with a Gaussian spectrum profile (458 to 612 nm), and the optical system is designed to measure light emitted from the fluid sample-applied zone or the pigment analyte-detection zone 107 (second detection zone) on the chromatography medium using silicon diode. A scanning system, similar to the fluorescence measurement system, is used, and all of the light reflected from the light source is measured in a short time.

A method for quantifying the antigen analyte in a sample using the lateral flow assay system according to the present invention will be also described in more detail with reference to Drawings.

FIG. 1 is a view showing the construction of the strip used in the lateral flow quantitative assay according to the present invention. The quantification of antigen analyte according to the present invention begins with the application of a fluid sample to the strip according to the present invention. The fluid sample is applied to the sample pad 102, preferably through a sample holder 109. When the sample is applied to the sample pad, it moves via capillary action, and its speed may vary depending on the quality and size of the absorption pad. At this time, when a detector is introduced to the sample before applying the sample or during migration, a primary immune response occurs to form a conjugate, which may be carried out by two methods. One method is as follows: after collecting a fluid sample from the sample, a predetermined amount of the labeled detector is directly added to the fluid sample before performing quantification, and thus the primary immune response between the antigen analyte in the fluid sample and the detector occurs. The resulting fluid sample is applied to the strip. The other alternative method is to apply the liquid sample to the strip including the conjugate releasing pad which is manufactured by adsorbing a fluorescently-labeled detector onto the conjugate releasing pad 103 in advance. In this regard, although the detector is adsorbed onto the conjugate releasing pad, it is solubilized in and/or mixed with a solvent or the liquid sample that is applied to the conjugate releasing pad, leading to the primary immune responses with the antigen analyte. Any of the methods may be employed, but the former method is preferable in that a variety of detectors can be conveniently applied for the analysis and total hemoglobin levels can be easily determined.

The detector is an antibody that will not bind to other pigment analyte in the fluid sample, but specifically bind to the antigen analyte, glycohemoglobin, and may be prepared according to the various methods disclosed prior to the date of the present application. Preferably, example thereof may be a mouse monoclonal antibody, but is not limited thereto. In addition, it is preferable to use a detector that is labeled with a fluorescent material as a signal generating source, regardless of the above described methods of introducing the detector to the sample.

The primary immune response results in the formation of a fluorescently-labeled detector-antigen analyte conjugate, which migrates along the chromatography medium 104, and the free detector, which does not bind with the antigen analyte, migrates along the strip to reach the antigen analyte-detection zone 106.

The antigen analyte-detection zone is located at a predetermined distance from the sample application site, namely, the sample pad, and a predetermined amount of captor is immobilized thereto. The captor may be glycohemoglobin or a compound capable of recognizing the detector, and is immobilized on the antigen analyte-detection zone. Therefore, the captor does not migrate along with the liquid sample, even though the liquid sample develops along the strip. When the sample containing the detector-antigen analyte conjugate and/or the free detector reaches to the area where the captor is immobilized, secondary immune response competitively occurs between the detector, the detector-antigen analyte conjugate, and the captor, and the laser-induced epifluorescence detection device collects signals generated by the fluorescently-labeled detector-captor conjugate in the captor-immobilized area (antigen analyte-detection zone).

The sample continuously moves along the strip to pass through the pigment analyte-detection zone 107. The pigment analyte-detection zone is not specifically defined, but any position on the strip can be considered, as long as the captor is not immobilized thereto. Preferably, the pigment analyte-detection zone may be any position that is exposed through a window 108 formed on the sample pad or a strip housing 110. In the pigment analyte-detection zone, total hemoglobin levels are measured by the LED responses to the red color of hemoglobin. Subsequently, the absorption pad 150 accommodates the sample passed through the antigen analyte-detection zone and the pigment analyte-detection zone.

In order to quantify the antigen analyte, a standard curve of hemoglobin and glycohemoglobin should be established, in which the whole blood is used, and its concentration may be determined by any methods known in the art. The prepared whole blood specimen is applied to the strip according to the present invention, and then fluorescence is measured using the laser-induced epifluorescence detection device to establish the standard curve.

Hereinafter, the present invention will be described in more detail by way of Examples. It is to be understood, however, that these examples are for illustrative purposes only are not construed to limit the scope of the present invention.

Example 1

Preparation of Protein-fluorescent Material Conjugate

A fluorescent material as a signal generating source was ligated to the mouse monoclonal antibody against an antigen analyte of interest, glycohemoglobin (HbA1c), as follows. Proteins to be used in binding of the fluorescent material were purified to a purity of at least 95%. The proteins were used at a concentration of at least 1 mg/ml for optimal binding. The purified proteins were dialyzed against a buffer solution (0.1 M sodium bicarbonate, pH 8.5) not containing ammonia or amine ions in a refrigerator at 4° C. for 12 to 24 hours in order to facilitate the reaction with the fluorescent material. The proteins dialyzed were kept in a freezer at −20° C. until use. The proteins dialyzed in the buffer solution were directly but slowly added to powdered Alexa 647 fluorescent material (Molecular Probes, USA) and the mixture was stirred for 1 to 2 hours in a refrigerator at 4° C.

Example 2

Purification of Protein-fluorescent Material Conjugate

Excess fluorescent material that did not react with the protein/fluorescent material conjugate was removed using a distribution column packed with Sephadex G-25. As a purifying buffer solution, 0.1 M sodium carbonate (pH 8.5) was used. The purified protein/fluorescent material conjugates were kept in a refrigerator or -20° C. freezer until use.

Example 3

Immobilization of Captor on Nitrocellulose Membrane

The captor, HbA1c was immobilized on a nitrocellulose membrane in a thin line shape using a Biodot dispenser while varying the concentration and amount. The membrane with immobilized proteins was stored in a dehumidifier kept at 25° C. and a humidity of 35 to 50% for 2 hours. Then, in order to stabilize the protein and prevent non-specific reactions between reagents, the membrane was treated with a stabilizing solution (1% BSA, 0.05% Tween20, 1% sucrose, 0.1% PVA) and equilibrated for 5 minutes. As the components of the stabilizing solution, BSA may be substituted with gelatin, Tween 20 may be substituted with Triton X-100, sucrose may be substituted with trehalose, PVA (polyvinylalcohol) may be substituted with PEG or PVP (polyvinylpyrrolidone). After removing excess solution, the membrane was dried at 40° C. for 30 minutes. The dry membrane was stored in an appropriate container kept at 25° C. and RH of 35 to 50% until use.

Example 4

Pretreatment of Sample Pad

The sample pad was pretreated in order to facilitate movement of components of a solution through the nitrocellulose membrane, to maintain a high sensitivity of reaction and to prevent experimental errors due to a non-specific reaction between protein/fluorescent material conjugate and a sample.

A sample pad (2.5×30 cm) was sufficiently wetted with a pretreating solution (20 mM Tris-Cl, 0.1% Triton X-100, 0.05% NaN3, pH 8.5) by repeatedly applying 1 ml of the solution and equilibrating for 10 minutes. When whole blood was used as a sample, another pretreating solution (PBS, 10 mM phosphate, 150 mM NaCl, 1% BSA, 0.05% Tween 20,0.05% NaN3, pH 7.4) was used to prevent hemolysis of red blood cells. After removing excess solution, the sample pad was vacuum dried at a temperature of 50° C. to 60° C. for 1 hour to prevent the pad deformation due to heat. The lyophilization method was selected to minimize denaturation of the protein/fluorescent material conjugate. The prepared pad was stored in an appropriate container under the same conditions as for the foregoing membrane.

Example 5

Manufacture of Fluorescence Immunochromatographic Assay Strip for Glycohemoglobin The nitrocellulose membrane (NC membrane), the sample pad, the absorption pad, and the backing card were assembled in a disposable cassette, so as to manufacture a strip having a size of 460 mm. The captor, human glycohemoglobin (2 mg/ml) was dispensed in an amount of 0.88 μl/cm in a line with a width of 0.8 mm on the NC membrane using the Bio Dot dispenser, and fixed at RH 35 to 50% for 2 hours. Then, the membrane was treated with a stabilizing solution (1% BSA, 0.05% Tween20, 0.1% PVA) for stabilization of proteins and prevention of non-specific reactions between reagents, and equilibrated for 5 minutes (as the components of the stabilizing solution, BSA may be substituted with gelatin, Tween 20 may be substituted with Triton X-100, sucrose may be substituted with trehalose, PVA may be substituted with PEG or PVP). After removing excess solution, the treated membrane was dried at 40° C. for 30 minutes. The membrane to be used in the experiment was assembled with the sample pad, the absorption pad, etc., and cut to a width of 4 mm using a cutter so that the final strip had a dimension of 4×60 mm.

Streptavidin (3 g/L) was dispensed at the control line of an internal standard on the NC membrane in an amount of 1 μl/cm in a line with a width of 1 mm using the Bio Dot dispenser (Irvine, Calif., USA). The manufactured strip was assembled in a disposable cassette (16×90 mm) that was designed to fit in a holder of laser-fluorescence scanner, and packed in a dehumidifier, followed by storage at room temperature until use.

Example 6

Preparation of Detector Buffer Solution

Instead of the method of immobilizing the detector on the conjugate releasing pad, which is generally used in the known lateral flow chromatography, the detector was stored in a new tube in a liquid state. The collected blood was no more than 5 μl, which is not enough to cause migration on the developing membrane. Thus, addition of a buffer solution was needed. The used buffer solution was PBS supplemented with 1% BSA.

Example 7

Preparation of Hemolytic Solution of Red Blood Cells 50 g of potassium ferricyanide was dissolved in 1 L of 10 mM Kpi solution, and 100 mg of digitonin was added thereto for hemolysis of red blood cells, so as to prepare a solution of pH 7.4. The prepared solution was sterilized using a 0.45 μm membrane filter, and stored at a cool, dark place until use.

Example 8

Construction of Hemoglobin Standard Curve Using LED Detection System

The whole blood, of which concentration had been measured by a known biochemical test, was used as a reference material for hemoglobin measurement. The prepared solution was applied to the strip for measuring glycohemoglobin, and the value of hemoglobin was measured in an apparatus that was manufactured for simultaneous measurement of glycohemoglobin and hemoglobin, followed by construction of standard curve. It was found that the hemoglobin concentration measured by silicon diode was completely consistent with that measured by the known biochemical test. The concentration-dependent results are shown in FIG. 4. There was a strong correlation (R2 value of 0.98 or higher) between the concentrations measured by the strip and by the known method. The CV % value that represents reproducibility was less than 3%, showing high reliability.

Example 9

Construction of Glycohemoglobin Standard Curve Using Immunochromatography

A BSA-biotin conjugate (0.1 g/L) and an anti-HbA1c antibody (4 μg/ml) were used to prepare a glycohemoglobin detection solution, and 0.25, 0.5, 1, and 2 mg/ml of glycohemoglobin were mixed with the detection solution at a ratio of 1:1, respectively. 75 μl of each mixture was added to the sample holder of the cassette. The cartridge, to which the mixed solution was applied, was reacted at room temperature for 12 minutes, and then fluorescence intensity was measured using a fluorescence detector. The results recorded on the test and control lines were converted into an area value (test line: $A_T$, control line: $A_C$) by the prepared program, and then the concentrations of antigens were calculated by the ratio ($A_T/A_C$) of the area value, shown in FIG. 5. As shown in FIG. 5, the area value was proportional to the glycohemoglobin concentration, in a concentration-dependent manner, and HbA1c % was calculated using the standard curve. As a result, there was a strong correlation (R value of 0.99) with HbA1c concentration. The low CV % value of 5% was found.

Example 10

Comparison Test in Specimen with Known HbA1c Measurement Apparatus

The glycohemoglobin value was determined using the HPL Bio-Rad Variant II, and then specimens were measured using the glycohemoglobin measurement system according to the present invention. The measured values were compared with each other. The result values were compared, and shown in FIG. 6. The immunoassay and HPLC methods used in the present invention are basically different from each other, but a strong correlation R value of 0.96 was found.

The integrated lateral flow quantitative assay system consisting of a lateral flow assay strip, a laser-induced epifluorescence detection device, and an LED detection device provide a method for effectively quantifying glycohemoglobin by antigen-antibody reaction, thereby being very useful for patients in need of strict management of glucose levels.

What is claimed is:
1. An assay system comprising:
an assay device comprising:
a pad configured to receive a sample and a detector for providing a mixture comprising the sample and the detector, the sample comprising glycohemoglobin and non-glycohemoglobin, the detector having specificity in binding with glycohemoglobin while having little specificity in binding with non-glycohemoglobin, wherein the detector is included in the mixture in a predetermined amount that is more than sufficient to bind with substantially all glycohemoglobin;
a strip comprising a chromatographic medium configured to receive the mixture from the pad and to let the mixture migrate in a direction in the chromatographic medium;
a first detection zone provided in the strip and distanced at a first predetermined distance from the pad in the direction, wherein the first detection zone comprises a captor having specificity in binding with the detector, wherein the captor is immobilized in the first detection zone and provided in an amount that is sufficient to capture substantially all the detector that are not bound with glycohemoglobin and reach the first detection zone, wherein the first detection zone provides an access for detecting an amount of the detector captured in the first detection zone; and
a second detection zone provided in the strip and distanced at a second predetermined distance from the pad in the direction, wherein the second detection zone provides an access for detecting an amount of non-glycohemoglobin and glycohemoglobin that are staying or passing in the second detection zone at a detection time;
a first detection device configured to irradiate first light beams to the first detection zone and to detect fluorescence from a fluorescent moiety bound to the detector in response to the first light beams; and
a second detection device configured to irradiate second light beams to the second detection zone and to detect light emitted from non-glycohemoglobin and glycohemoglobin in response to the second light beams.

2. The system of claim 1, wherein the detector further comprises a fluorescent moiety, wherein the access of the first detection zone is configured to make available detection of fluorescence of the fluorescent moiety in response to first light beams irradiated to the first detection zone.

3. The system of claim 1, wherein the access of the second detection zone is configured to make available detection of light emitted from non-glycohemoglobin and glycohemoglobin in response to second light beams irradiated to the second detection zone.

4. The system of claim 1, wherein the pad is configured to receive the sample and the detector in a pre-mixed form.

5. The system of claim 1, wherein the pad comprises a sample receiving portion for receiving the sample and a detector receiving portion for receiving the detector, wherein the pad is further configured to mix the received sample and detector therein.

6. The system of claim 1, wherein the detector comprises a glycohemoglobin—binding site that is specific in binding with glycohemoglobin, wherein the captor has specificity in binding with the glycohemoglobin—binding site of the detector.

7. The system of claim 1, wherein the first detection zone extends in a first length from the first distance in the direction, and the second detection zone extends in a second length from the second distance in the direction.

8. The system of claim 1, wherein the first detection zone and the second detection zone at least partly overlap with each other.

9. The system of claim 1, wherein the first detection zone and the second detection zone do not overlap with each other.

10. The system of claim 1, wherein the first and second detection devices are arranged and configured relative to each other such that the first detection device irradiates the first light beams to the first detection zone and that simultaneously or sequentially the second detection device irradiates the second light beams to the second detection zone without having to move the assay device relative to one of the first and second detection devices.

11. The system of claim 1, wherein the first detection device comprises a first light source and a first sensor, which are integrated in a single piece or provided in separate pieces, and wherein the second detection device comprises a second light source and a second sensor, which are integrated in a single piece or provided in separate pieces.

12. An assay method comprising:
providing an assay device comprising:
a pad configured to receive a sample and a detector for providing a mixture comprising the sample and the detector, the sample comprising glycohemoglobin and non-glycohemoglobin, the detector having specificity in binding with glycohemoglobin while having little specificity in binding with non-glycohemoglobin, wherein the detector is included in the mixture in a predetermined amount that is more than sufficient to bind with substantially all glycohemoglobin;
a strip comprising a chromatographic medium configured to receive the mixture from the pad and to let the mixture migrate in a direction in the chromatographic medium;
a first detection zone provided in the strip and distanced at a first predetermined distance from the pad in the direction, wherein the first detection zone comprises a captor having specificity in binding with the detector, wherein the captor is immobilized in the first detection zone and provided in an amount that is sufficient to capture substantially all the detector that are not bound with glycohemoglobin and reach the first detection zone, wherein the first detection zone provides an access for detecting an amount of the detector captured in the first detection zone; and
a second detection zone provided in the strip and distanced at a second predetermined distance from the pad in the direction, wherein the second detection zone provides an access for detecting an amount of non-glycohemoglobin and glycohemoglobin that are staying or passing in the second detection zone at a detection time;
providing, in the pad, a mixture comprising glycohemoglobin in an unknown amount, non-glycohemoglobin in an unknown amount and a detector in a predetermined amount, the detector having specificity in binding with glycohemoglobin while having little specificity in binding with non-glycohemoglobin, wherein the detector is included in the mixture in a predetermined amount that is more than sufficient to bind with substantially all glycohemoglobin in the mixture;
permitting the mixture to migrate in the chromatographic medium of the strip in the direction away from the pad, wherein substantially all the detector that are not bound with glycohemoglobin are captured in the first detection zone upon reaching the first detection zone;
measuring an amount of the detector captured in the first detection zone; and
measuring an amount of the non-glycohemoglobin and glycohemoglobin that are staying or passing in the second detection zone at a detection time, which is past a period after initial migration of the mixture in the strip.

13. The method of claim 12, further comprising:
computing the unknown amount of glycohemoglobin contained in the mixture using the measured amount of the detector captured in the first detection zone and further using the predetermined amount of the detector.

14. The method of claim 12, further comprising:
determining a total amount of glycohemoglobin and non-glycohemoglobin contained in the mixture using the measured amount of the non-glycohemoglobin and glycohemoglobin in the second detection zone and further using reference data of migration of non-glycohemoglobin and glycohemoglobin in the chromatographic medium, wherein the reference data comprises a hemoglobin standard curve.

15. The method of claim 12, further comprising:
computing the unknown amount of glycohemoglobin contained in the mixture, wherein computing comprises subtracting measured amount of the detector captured in the first detection zone from the predetermined amount of the detector;
computing a total amount of glycohemoglobin and non-glycohemoglobin contained in the mixture using the measured amount of the non-glycohemoglobin and glycohemoglobin in the second detection zone; and
computing a ratio of the computed amount of glycohemoglobin and the computed total amount of glycohemoglobin and non-glycohemoglobin contained in the mixture.

16. The method of claim 12, wherein the detector further comprises a fluorescent moiety, wherein measuring an amount of the detector comprises:
irradiating first light beams to the first detection zone; and
detecting fluorescence of the fluorescent moiety in response to the first light beams.

17. The method of claim 12, wherein measuring an amount of the non-glycohemoglobin and glycohemoglobin comprises:
irradiating second light beams to the second detection zone; and
detecting light emitted from non-glycohemoglobin and glycohemoglobin in response to the second light beams at the detection time.

18. The method of claim 12, wherein measuring an amount of the detector comprises using a first detection device comprising a first light source and a first sensor, wherein measuring an amount of the non-glycohemoglobin and glycohemoglobin comprises using a second detection device comprising a second light source and a second detector, wherein the first and second detection devices are arranged and configured relative to each other such that the first detection device irradiates first light beams to the first detection zone and that simultaneously or sequentially the second detection device irradiates second light beams to the second detection zone without having to move the assay device relative to one of the first and second detection devices.

19. The method of claim 12, wherein the detector comprises a glycohemoglobin-binding site that is specific in binding with glycohemoglobin, wherein the captor has specificity in binding with the glycohemoglobin-binding site of the detector.

* * * * *